United States Patent
Silver

(10) Patent No.: US 10,548,747 B2
(45) Date of Patent: Feb. 4, 2020

(54) LOWER LIMB PROSTHETIC DEVICE

(71) Applicant: Daniel M. Silver, Encino, CA (US)

(72) Inventor: Daniel M. Silver, Encino, CA (US)

(*) Notice: Subject to any disclaimer, the term of this patent is extended or adjusted under 35 U.S.C. 154(b) by 106 days.

(21) Appl. No.: 15/803,326

(22) Filed: Nov. 3, 2017

(65) Prior Publication Data

US 2019/0133792 A1     May 9, 2019

(51) Int. Cl.
| | | |
|---|---|---|
| *A61F 2/62* | (2006.01) | |
| *A61F 2/66* | (2006.01) | |
| *A61F 2/80* | (2006.01) | |
| *A61F 2/78* | (2006.01) | |
| *A61F 2/60* | (2006.01) | |
| *A61F 2/76* | (2006.01) | |
| *A61F 2/50* | (2006.01) | |
| *A61F 2/68* | (2006.01) | |

(52) U.S. Cl.
CPC .............. *A61F 2/7843* (2013.01); *A61F 2/60* (2013.01); *A61F 2/76* (2013.01); *A61F 2/68* (2013.01); *A61F 2/80* (2013.01); *A61F 2002/502* (2013.01); *A61F 2002/5018* (2013.01); *A61F 2002/5084* (2013.01); *A61F 2002/5089* (2013.01); *A61F 2002/665* (2013.01); *A61F 2002/6614* (2013.01); *A61F 2220/0025* (2013.01)

(58) Field of Classification Search
CPC .................... A61F 2/7843; A61F 2/602; A61F 2002/5001; A61F 2002/502; A61F 2002/5084; A61F 2002/5089; A61F 2002/509; A61F 2002/6614; A61F 2002/665
See application file for complete search history.

(56) References Cited

U.S. PATENT DOCUMENTS

| | | | | |
|---|---|---|---|---|
| 49,234 | A * | 8/1865 | Coombs | .................... A61F 2/80 623/37 |
| 2,229,575 | A | 1/1941 | Kaplan | |
| 2,634,424 | A * | 4/1953 | O'Gorman | ............ A61F 2/7843 623/37 |
| 3,633,967 | A | 1/1972 | Timmins | |
| 4,459,709 | A | 7/1984 | Leal et al. | |
| D282,006 | S | 12/1985 | Marsh et al. | |
| 4,923,475 | A * | 5/1990 | Gosthnian | ............. A61F 2/7843 623/37 |

(Continued)

FOREIGN PATENT DOCUMENTS

FR     3 071 717 A1 *   4/2019  ............... A61F 2/42

*Primary Examiner* — David H Willse

(57) ABSTRACT

A lower limb prosthetic device for use when bathing and showering includes a first shell. A rod is coupled to and extends substantially perpendicularly from an upper face of the first shell. A second shell, which has a top that is open, is coupled to and extends from the rod distal from the first shell. The second shell is substantially complementary to and configured to insert a stump of an amputated leg. A plurality of bladders, which is selectively inflatable, is coupled to an inner surface of the second shell. The bladders are configured to be inflated to couple the second shell to the stump. A plurality of first holes and a plurality of second holes are positioned through the first shell and the second shell, respectively. The first holes and the second holes are configured to drain water from the first shell and the second shell, respectively.

16 Claims, 5 Drawing Sheets

(56) References Cited

U.S. PATENT DOCUMENTS

| | | |
|---|---|---|
| 9,192,486 B2 | 11/2015 | Rauch |
| 9,539,119 B2 | 1/2017 | Sauer |
| 2011/0320010 A1 | 12/2011 | Vo |
| 2016/0324666 A1* | 11/2016 | Barberio ............... A61F 2/7812 |

* cited by examiner

LOWER LIMB PROSTHETIC DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to prosthetic devices and more particularly pertains to a new prosthetic device for use when bathing and showering.

BRIEF SUMMARY OF THE INVENTION

An embodiment of the disclosure meets the needs presented above by generally comprising a first shell. A rod is coupled to and extends substantially perpendicularly from an upper face of the first shell. A second shell, which has a top that is open, is coupled to and extends from the rod distal from the first shell. The second shell is substantially complementary to and configured to insert a stump of an amputated leg. A plurality of bladders, which is selectively inflatable, is coupled to an inner surface of the second shell. The bladders are configured to be inflated to couple the second shell to the stump. A plurality of first holes and a plurality of second holes are positioned through the first shell and the second shell, respectively. The first holes and the second holes are configured to drain water from the first shell and the second shell, respectively.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
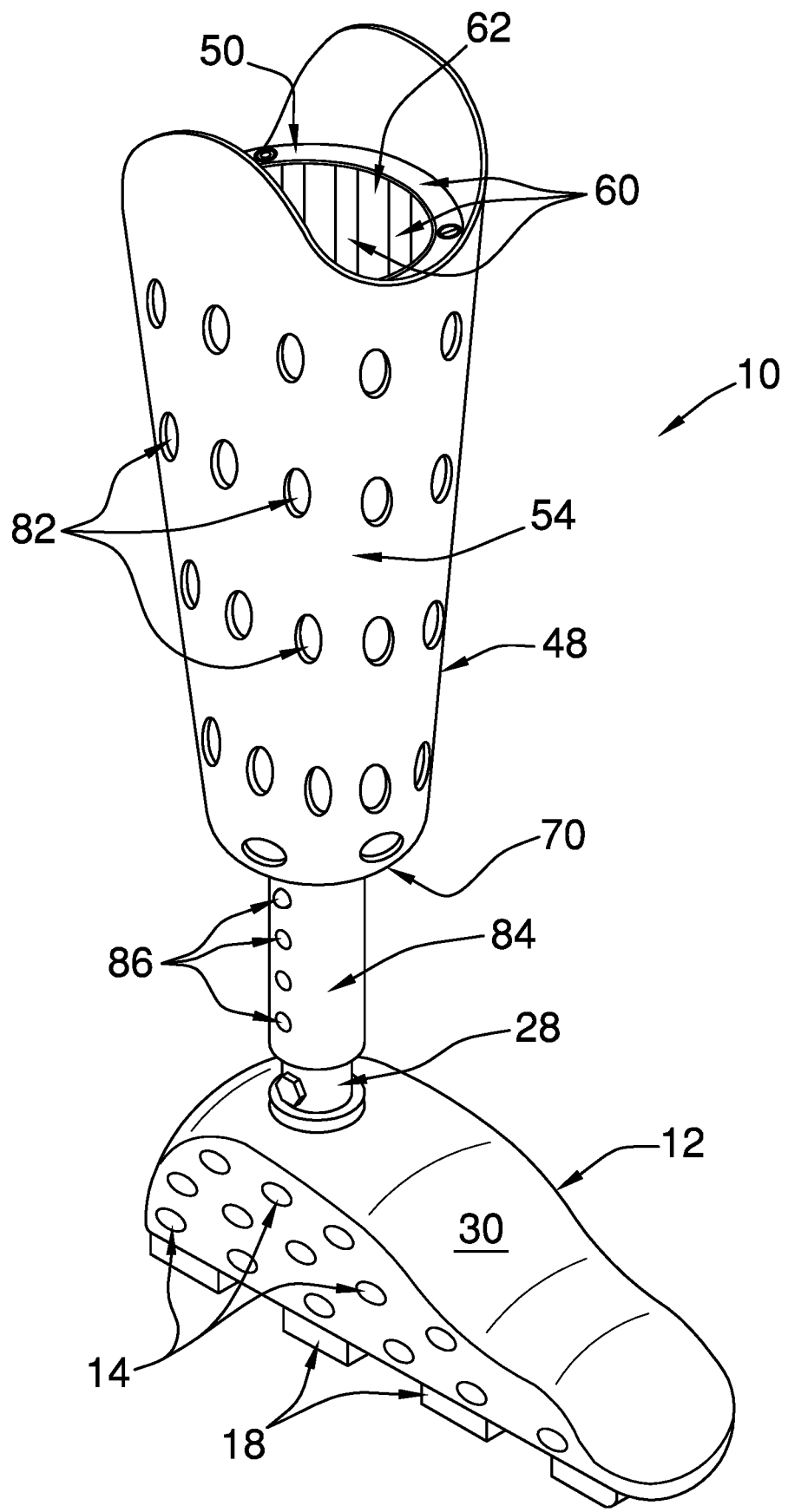
FIG. 1 is an isometric perspective view of a lower limb prosthetic device according to an embodiment of the disclosure.
Figure 2:
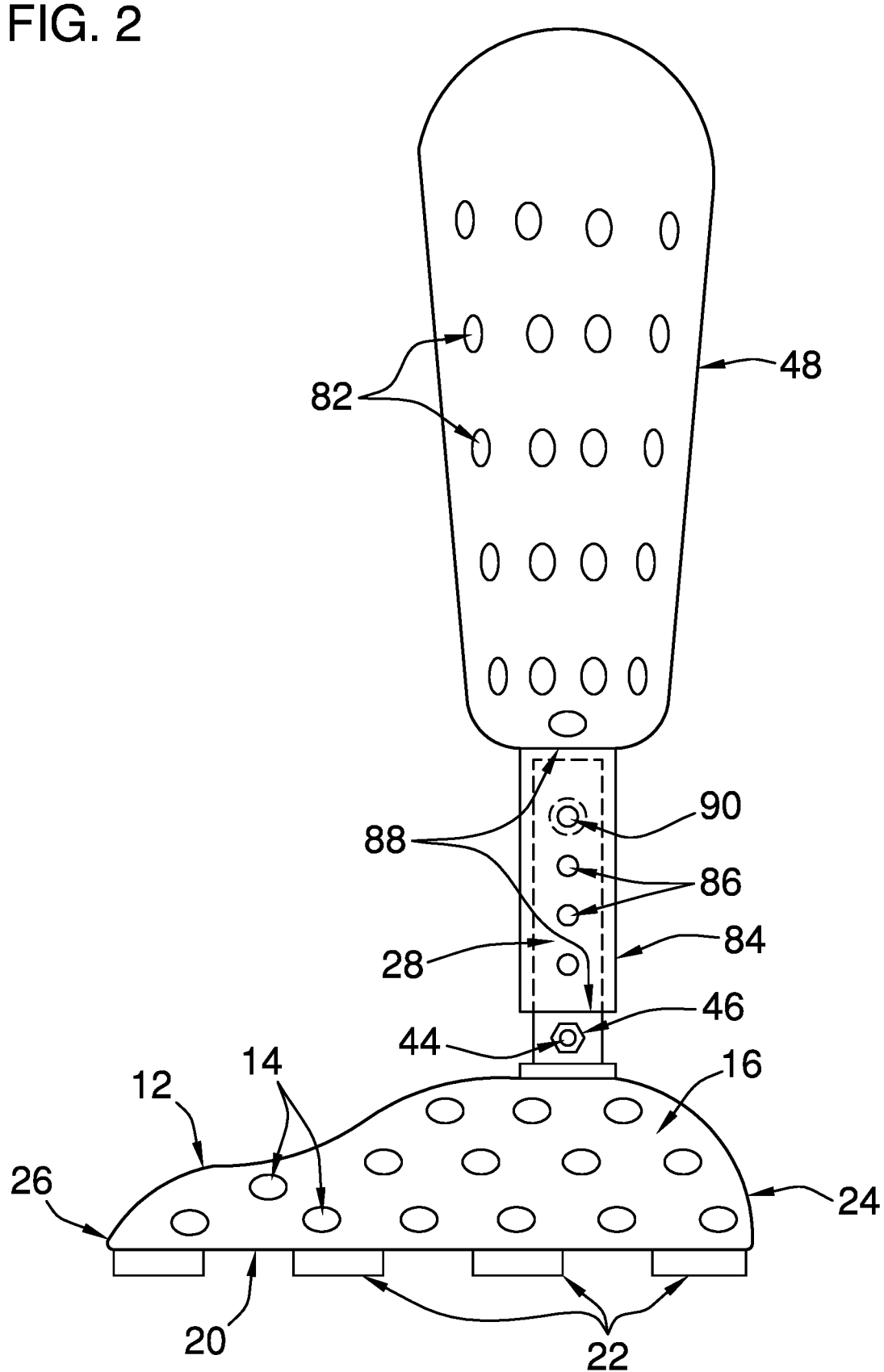
FIG. 2 is a side view of an embodiment of the disclosure.
Figure 3:
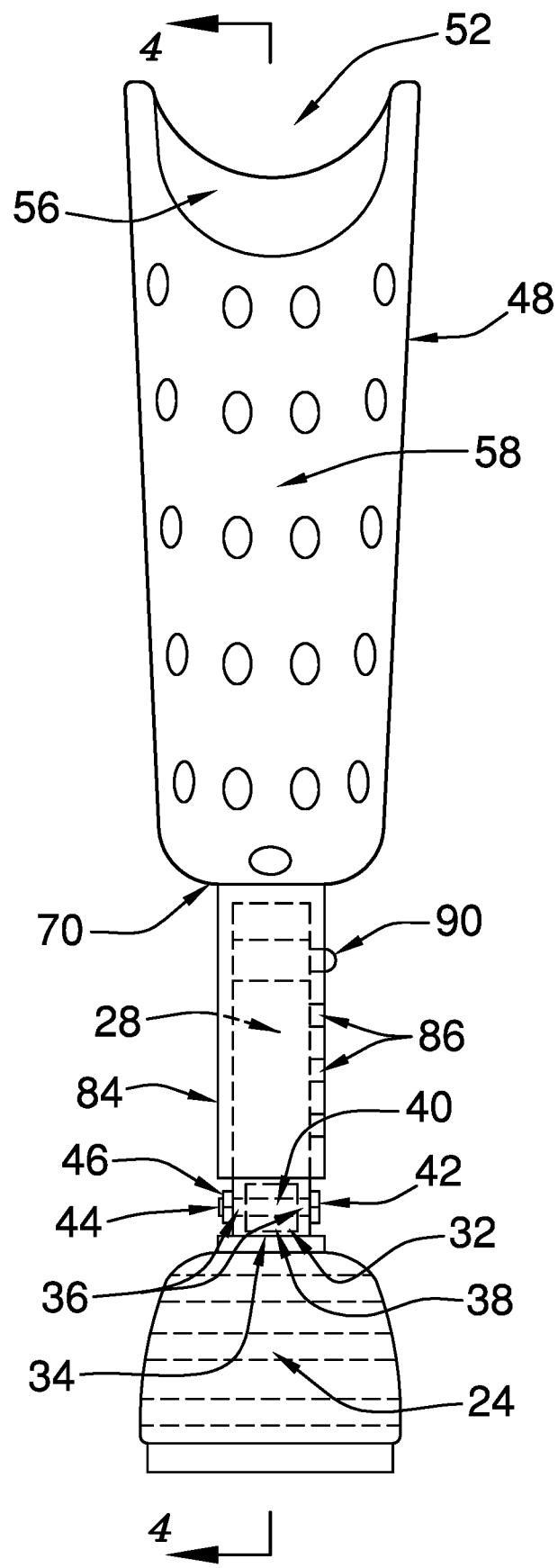
FIG. 3 is a rear view of an embodiment of the disclosure.
Figure 4:
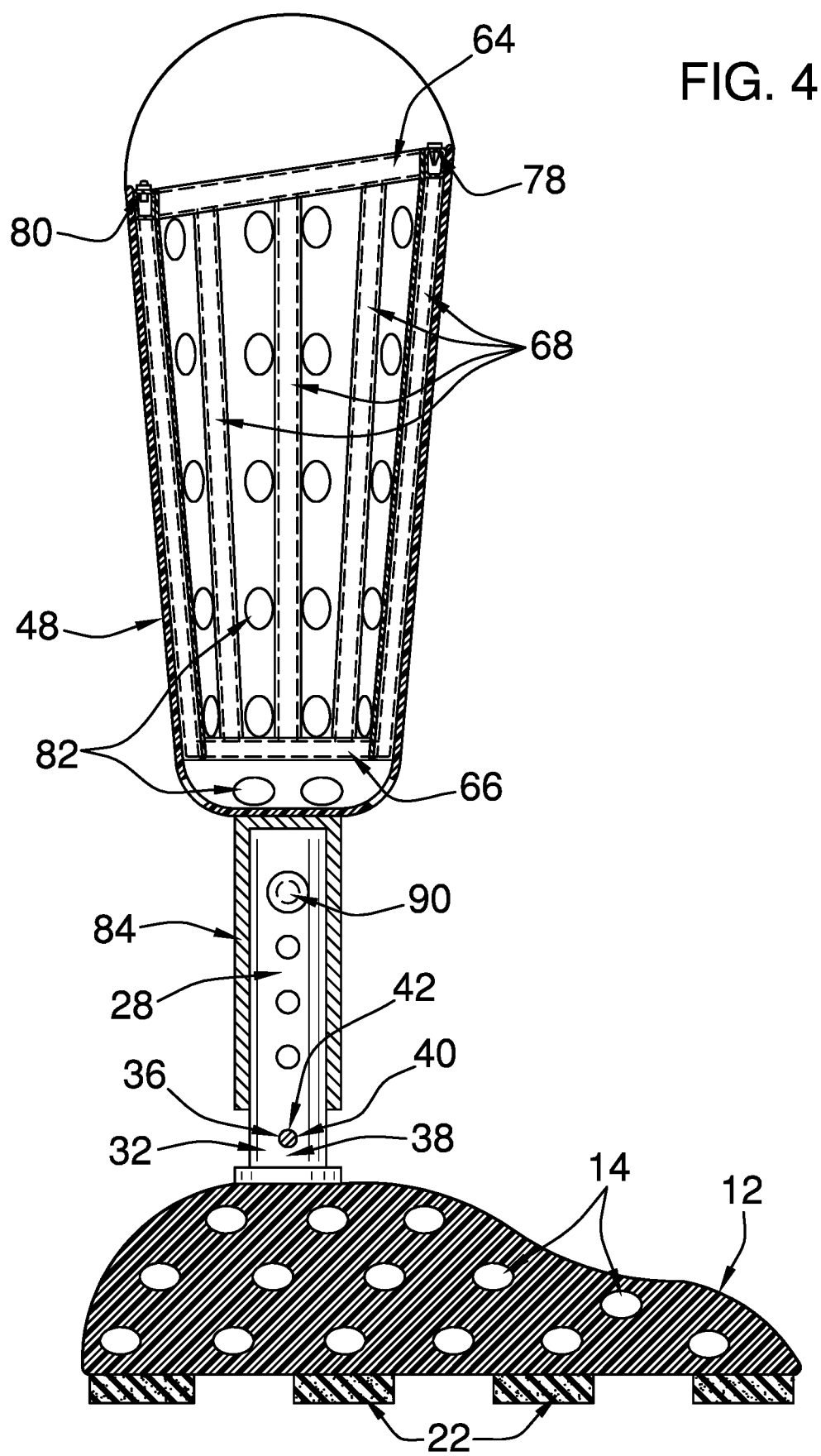
FIG. 4 is a cross-sectional view of an embodiment of the disclosure.
Figure 5:
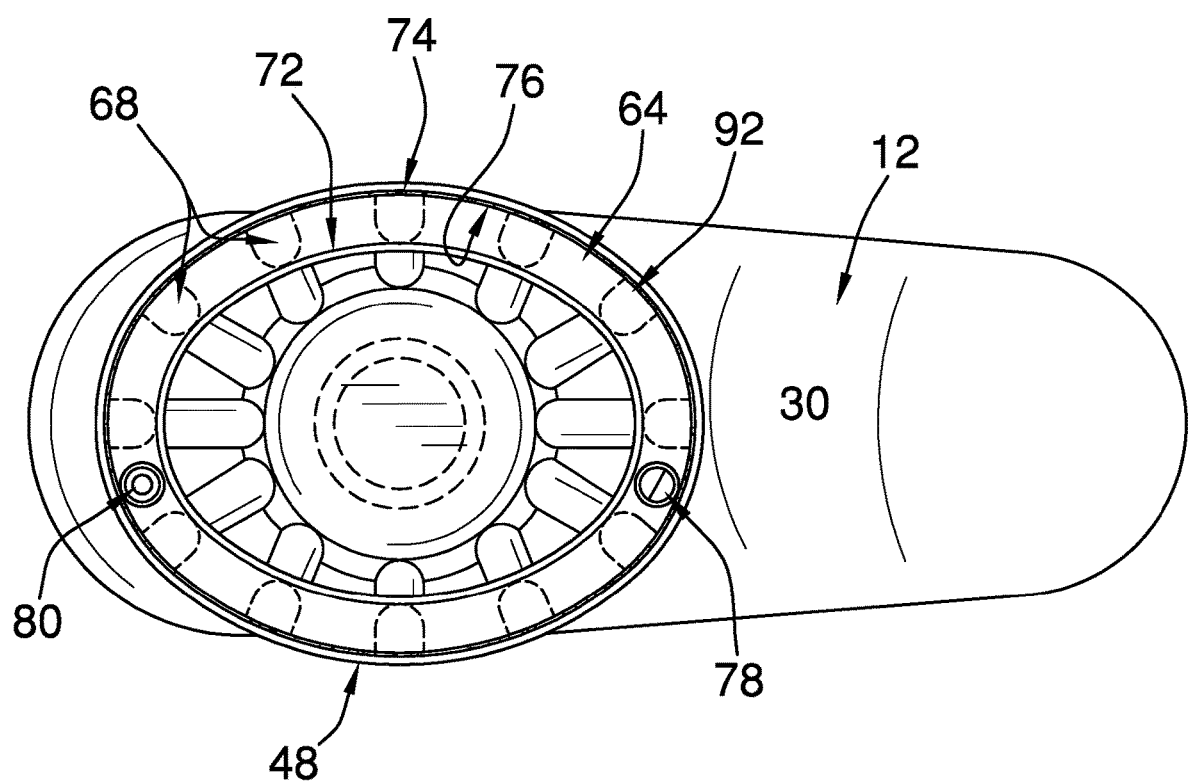
FIG. 5 is a top view of an embodiment of the disclosure.

With reference now to the drawings, and in particular to FIGS. 1 through 5 thereof, a new prosthetic device embodying the principles and concepts of an embodiment of the disclosure and generally designated by the reference numeral 10 will be described.

As best illustrated in FIGS. 1 through 5, the lower limb prosthetic device 10 generally comprises a first shell 12. A plurality of first holes 14 is positioned through opposing sides 16 of the first shell 12. The first holes 14 are configured to drain water from the first shell 12. In one embodiment, the first shell 12 is substantially shoe-shaped when viewed from a respective opposing side 16 of the first shell 12.

A grip 18 is coupled to a lower face 20 of the first shell 12. The grip 18 is configured to prevent slipping of the first shell 12 on a surface, such as a bathtub and a shower enclosure. In one embodiment, the grip 18 comprises a plurality of pads 22. The pads 22 comprise rubber. In another embodiment, the plurality of pads 22 comprises four pads 22. Each pad 22 extends between the opposing sides 16 of the first shell 12. The plurality of pads 22 is substantially evenly spaced between a heel end 24 and a toe end 26 of the first shell 12.

A rod 28 is coupled to and extends substantially perpendicularly from an upper face 30 of the first shell 12. In one embodiment, a first channel 32 extends into the rod 28 from a lower end 34 of the rod 28. Each of a pair of penetrations 36 is positioned in the rod 28 and extends to the first channel 32. The penetrations 36 are opposingly positioned in the rod 28. A shaft 38 is coupled to and extends from the first shell 12. The first channel 32 is positioned to insert the shaft 38. A second channel 40 is positioned through the shaft 38 distal from the first shell 12. The second channel 40 is complementary to and alignable with the pair of penetrations 36 to permit insertion of a bolt 42 that is complementary to the penetrations 36 and the second channel 40. A threaded end 44 of the bolt 42 is positioned to threadedly couple to a nut 46 to couple the shaft 38 to the rod 28.

A second shell 48 is coupled to and extends from the rod 28 distal from the first shell 12. The second shell 48 has a top 50 that is open. The second shell 48 is substantially complementary to a stump of an amputated leg. The second shell 48 is configured to insert the stump through the top 50.

A first cutout 52 extends into a front 54 of the second shell 48 from the top 50. The first cutout 52 is arcuate. The first cutout 52 is configured to insert a patella and a femoral condyle of the amputated leg.

A second cutout 56 extends into a back 58 of the second shell 48 from the top 50. The second cutout 56 is arcuate. The second cutout 56 is dimensionally larger than the first cutout 52. The second cutout 56 is configured to allow flexing of a knee of the amputated leg.

A plurality of bladders 60 is coupled to an inner surface 62 of the second shell 48. The bladders 60 are selectively inflatable. The bladders 60 are configured to be inflated to couple the second shell 48 to the stump that is positioned in the second shell 48. In one embodiment, the bladders 60 are reversibly couplable to the second shell 48.

In another embodiment, the plurality of bladders 60 comprises a first tube 64, a second tube 66, and a plurality of third tubes 68. The first tube 64 extends annularly around the inner surface 62 proximate to the top 50 of the second shell 48. The second tube 66 extends annularly around the inner surface 62 proximate to a bottom 70 of the second shell 48. Each third tube 68 is fluidically coupled to and extends between the first tube 64 and the second tube 66. In yet another embodiment, the plurality of third tubes 68 comprises from four to twelve third tubes 68. In still yet another embodiment, the plurality of third tubes 68 comprises from eight to ten third tubes 68.

A sleeve 72 is coupled to the plurality of bladders 60. The sleeve 72 is substantially water impermeable. The sleeve 72 is configured to insert the stump to position the bladders 60 to be inflated to sealably couple the sleeve 72 to the stump.

A pair of first connectors 74 is coupled to the inner surface 62 of the second shell 48. A pair of second connectors 76 is coupled singly to the first tube 64 and the second tube 66. The second connectors 76 are complementary to the first connectors 74. Each second connector 76 is positioned to selectively couple to an associated first connector 74 to couple the plurality of bladders 60 to the second shell 48. In one embodiment, each second connector 76 and the associated first connector 74 comprise a hook and loop fastener 92.

An inlet valve 78 is positioned in the first tube 64. The inlet valve 78 is configured to couple to a pump to position the pump to inflate the plurality of bladders 60 to couple the second shell 48 to the stump that is positioned in the second shell 48.

An outlet valve 80 is positioned in the first tube 64. The outlet valve 80 is configured to release air from the plurality of bladders 60 to decouple the second shell 48 from the stump that is positioned in the second shell 48.

A plurality of second holes 82 is positioned through the second shell 48. The second holes 82 are configured to drain water from the second shell 48.

In one embodiment, a fourth tube 84 is coupled to the bottom 70 of the second shell 48. The fourth tube 84 is complementary to the rod 28. A plurality of orifices 86 is positioned through the fourth tube 84. The orifices 86 extend linearly between opposing ends 88 of the fourth tube 84. A pin 90 is coupled to and extends from the rod 28. The pin 90 is spring-loaded. The pin 90 is complementary to the orifices 86. Each orifice 86 is positioned to selectively insert the pin 90 to couple the fourth tube 84 to the rod 28 to fixedly position the second shell 48 relative to the first shell 12.

In use, the first channel 32 is positioned to insert the shaft 38. The second channel 40 is positioned to align with the pair of penetrations 36. The bolt 42 is positioned to be inserted through the second channel 40 and the penetrations 36. The threaded end 44 of the bolt 42 is positioned to threadedly couple to the nut 46 to couple the shaft 38 to the rod 28. Each orifice 86 is positioned to selectively insert the pin 90 to couple the fourth tube 84 to the rod 28 to fixedly position the second shell 48 relative to the first shell 12. Each second connector 76 is positioned to selectively couple to the associated first connector 74 to couple the plurality of bladders 60 to the second shell 48. The second shell 48 is configured to insert the stump through the top 50 into the sleeve 72. The inlet valve 78 is configured to couple to the pump to position the pump to inflate the plurality of bladders 60 to couple the second shell 48 to the stump that is positioned in the second shell 48. The outlet valve 80 is configured to release the air from the plurality of bladders 60 to decouple the second shell 48 from the stump that is positioned in the second shell 48. The first holes 14 are configured to drain water from the first shell 12. The second holes 82 are configured to drain water from the second shell 48. The grip 18 that is positioned on the first shell 12 is configured to prevent slipping of the first shell 12 on the surface, such as the bathtub and the shower enclosure. The first cutout 52 that is positioned in the second shell 48 is configured to insert the patella and the femoral condyle of the amputated leg. The second cutout 56 that is positioned in the second shell 48 is configured to allow flexing of the knee of the amputated leg.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A lower limb prosthetic device comprising:
   a first shell;
   a plurality of first holes positioned through opposing sides of said first shell;
   a rod coupled to and extending substantially perpendicularly from an upper face of said first shell;
   a second shell coupled to and extending from said rod distal from said first shell, said second shell having a top, said top being open, said second shell being substantially complementary to a stump of an amputated leg;
   a plurality of bladders coupled to an inner surface of said second shell, said bladders being selectively inflatable;
   a plurality of second holes positioned through said second shell;
   wherein said first holes are positioned in said first shell such that said first holes are configured for draining water from said first shell, wherein said second shell is positioned on said rod such that said second shell is configured for inserting the stump through said top, wherein said bladders are positioned in said second shell such that said bladders are configured for inflating for coupling said second shell to the stump positioned in said second shell, wherein said second holes are positioned in said second shell such that said second holes are configured for draining water from said second shell;
a first channel extending into said rod from a lower end of said rod;
a pair of penetrations positioned in said rod and extending to said first channel, said penetrations being opposingly positioned in said rod;
a shaft coupled to and extending from said first shell;
a second channel positioned through said shaft distal from said first shell, said second channel being complementary to and alignable with said pair of penetrations;
a bolt complementary to said penetrations and said second channel; and
wherein said first channel is positioned in said rod such that said first channel is positioned for inserting said shaft such that said second channel is positioned for aligning with said pair of penetrations positioning said bolt for inserting through said second channel and said penetrations positioning a threaded end of said bolt for threadedly coupling to a nut for coupling said shaft to said rod.

2. The device of claim 1, further including said first shell being substantially shoe-shaped when viewed from a respective said opposing side of said first shell.

3. The device of claim 1, further including a grip coupled to a lower face of said first shell, wherein said grip is positioned on said first shell such that said grip is configured for preventing slipping of said first shell on a surface, such as a bathtub and a shower enclosure.

4. The device of claim 3, further including said grip comprising a plurality of pads, said pads comprising rubber.

5. The device of claim 4, further including said plurality of pads comprising four said pads, each said pad extending between said opposing sides of said first shell, said plurality of pads being substantially evenly spaced between a heel end and a toe end of said first shell.

6. The device of claim 1, further comprising:
a first cutout extending into a front of said second shell from said top, said first cutout being arcuate;
a second cutout extending into a back of said second shell from said top, said second cutout being arcuate, said second cutout being dimensionally larger than said first cutout; and
wherein said first cutout is positioned in said second shell such that said first cutout is configured for inserting a patella and a femoral condyle of the amputated leg, wherein said second cutout is positioned in said second shell such that said second cutout is configured for flexing of a knee of the amputated leg.

7. The device of claim 1, further including said bladders being reversibly couplable to said second shell.

8. The device of claim 1, further including said plurality of bladders comprising:
a first tube extending annularly around said inner surface proximate to said top of said second shell;
a second tube extending annularly around said inner surface proximate to a bottom of said second shell; and
a plurality of third tubes, each said third tube being fluidically coupled to and extending between said first tube and said second tube.

9. The device of claim 8, further including said plurality of third tubes comprising from four to twelve said third tubes.

10. The device of claim 9, further including said plurality of third tubes comprising from eight to ten said third tubes.

11. The device of claim 8, further comprising:
a pair of first connectors coupled to said inner surface of said second shell;
a pair of second connectors coupled singly to said first tube and said second tube, said second connectors being complementary to said first connectors; and
wherein said second connectors are positioned on said plurality of bladders such that each said second connector is positioned for selectively coupling to an associated said first connector for coupling said plurality of bladders to said second shell.

12. The device of claim 11, further including each said second connector and said associated said first connector comprising a hook and loop fastener.

13. The device of claim 8, further comprising:
an inlet valve positioned in said first tube;
an outlet valve positioned in said first tube; and
wherein said inlet valve is positioned in said first tube such that said inlet valve is configured for coupling to a pump positioning the pump for inflating said plurality of bladders for coupling said second shell to the stump positioned in said second shell, wherein said outlet valve is positioned in said first tube such that said outlet valve is configured for releasing air from said plurality of bladders for decoupling said second shell from the stump positioned in said second shell.

14. The device of claim 1, further including a sleeve coupled to said plurality of bladders, said sleeve being substantially water impermeable, wherein said sleeve is positioned on said bladders such that said sleeve is configured for inserting the stump positioning said bladders for inflating for sealably coupling said sleeve to the stump.

15. A lower limb prosthetic device comprising:
a first shell;
a plurality of first holes positioned through opposing sides of said first shell;
a rod coupled to and extending substantially perpendicularly from an upper face of said first shell;
a second shell coupled to and extending from said rod distal from said first shell, said second shell having a top, said top being open, said second shell being substantially complementary to a stump of an amputated leg;
a plurality of bladders coupled to an inner surface of said second shell, said bladders being selectively inflatable, said plurality of bladders comprising a first tube, a second tube, and a plurality of third tubes;
a plurality of second holes positioned through said second shell;
wherein said first holes are positioned in said first shell such that said first holes are configured for draining water from said first shell, wherein said second shell is positioned on said rod such that said second shell is configured for inserting the stump through said top, wherein said bladders are positioned in said second shell such that said bladders are configured for inflating for coupling said second shell to the stump positioned in said second shell, wherein said second holes are positioned in said second shell such that said second holes are configured for draining water from said second shell;

a fourth tube coupled to a bottom of said second shell, said fourth tube being complementary to said rod;
a plurality of orifices positioned through said fourth tube, said orifices extending linearly between opposing ends of said fourth tube;
a pin coupled to and extending from said rod, said pin being spring-loaded, said pin being complementary to said orifices; and
wherein said pin is positioned on said rod such that each said orifice is positioned for selectively inserting said pin for coupling said fourth tube to said rod for fixedly positioning said second shell relative to said first shell.

16. A lower limb prosthetic device comprising:
a first shell, said first shell being substantially shoe-shaped when viewed from a respective opposing side of said first shell;
a plurality of first holes positioned through said opposing sides of said first shell, wherein said first holes are positioned in said first shell such that said first holes are configured for draining water from said first shell;
a grip coupled to a lower face of said first shell, wherein said grip is positioned on said first shell such that said grip is configured for preventing slipping of said first shell on a surface, such as a bathtub and a shower enclosure, said grip comprising a plurality of pads, said pads comprising rubber, said plurality of pads comprising four said pads, each said pad extending between said opposing sides of said first shell, said plurality of pads being substantially evenly spaced between a heel end and a toe end of said first shell;
a rod coupled to and extending substantially perpendicularly from an upper face of said first shell;
a first channel extending into said rod from a lower end of said rod;
a pair of penetrations positioned in said rod and extending to said first channel, said penetrations being opposingly positioned in said rod;
a shaft coupled to and extending from said first shell;
a second channel positioned through said shaft distal from said first shell, said second channel being complementary to and alignable with said pair of penetrations;
a bolt complementary to said penetrations and said second channel, wherein said first channel is positioned in said rod such that said first channel is positioned for inserting said shaft such that said second channel is positioned for aligning with said pair of penetrations positioning said bolt for inserting through said second channel and said penetrations positioning a threaded end of said bolt for threadedly coupling to a nut for coupling said shaft to said rod;
a second shell coupled to and extending from said rod distal from said first shell, said second shell having a top, said top being open, said second shell being substantially complementary to a stump of an amputated leg, wherein said second shell is positioned on said rod such that said second shell is configured for inserting the stump through said top;
a first cutout extending into a front of said second shell from said top, said first cutout being arcuate, wherein said first cutout is positioned in said second shell such that said first cutout is configured for inserting a patella and a femoral condyle of the amputated leg;
a second cutout extending into a back of said second shell from said top, said second cutout being arcuate, said second cutout being dimensionally larger than said first cutout, wherein said second cutout is positioned in said second shell such that said second cutout is configured for flexing of a knee of the amputated leg;
a plurality of bladders coupled to an inner surface of said second shell, said bladders being selectively inflatable, wherein said bladders are positioned in said second shell such that said bladders are configured for inflating for coupling said second shell to the stump positioned in said second shell, said bladders being reversibly couplable to said second shell, said plurality of bladders comprising:
 a first tube extending annularly around said inner surface proximate to said top of said second shell,
 a second tube extending annularly around said inner surface proximate to a bottom of said second shell, and
 a plurality of third tubes, each said third tube being fluidically coupled to and extending between said first tube and said second tube, said plurality of third tubes comprising from four to twelve said third tubes, said plurality of third tubes comprising from eight to ten said third tubes;
a sleeve coupled to said plurality of bladders, said sleeve being substantially water impermeable, wherein said sleeve is positioned on said bladders such that said sleeve is configured for inserting the stump positioning said bladders for inflating for sealably coupling said sleeve to the stump;
a pair of first connectors coupled to said inner surface of said second shell;
a pair of second connectors coupled singly to said first tube and said second tube, said second connectors being complementary to said first connectors, wherein said second connectors are positioned on said plurality of bladders such that each said second connector is positioned for selectively coupling to an associated said first connector for coupling said plurality of bladders to said second shell, each said second connector and said associated said first connector comprising a hook and loop fastener;
an inlet valve positioned in said first tube, wherein said inlet valve is positioned in said first tube such that said inlet valve is configured for coupling to a pump positioning the pump for inflating said plurality of bladders for coupling said second shell to the stump positioned in said second shell;
an outlet valve positioned in said first tube, wherein said outlet valve is positioned in said first tube such that said outlet valve is configured for releasing air from said plurality of bladders for decoupling said second shell from the stump positioned in said second shell;
a plurality of second holes positioned through said second shell, wherein said second holes are positioned in said second shell such that said second holes are configured for draining water from said second shell;
a fourth tube coupled to said bottom of said second shell, said fourth tube being complementary to said rod;
a plurality of orifices positioned through said fourth tube, said orifices extending linearly between opposing ends of said fourth tube;
a pin coupled to and extending from said rod, said pin being spring-loaded, said pin being complementary to said orifices, wherein said pin is positioned on said rod such that each said orifice is positioned for selectively inserting said pin for coupling said fourth tube to said rod for fixedly positioning said second shell relative to said first shell; and wherein said first channel is positioned in said rod such that said first channel is positioned for inserting said shaft such that said second channel is positioned for aligning with said pair of penetrations positioning said bolt for inserting through said second channel and said penetrations positioning said threaded end of said bolt for threadedly coupling to said nut for coupling said shaft to said rod, wherein said pin is positioned on said rod such that each said orifice is positioned for selectively inserting said pin for coupling said fourth tube to said rod for fixedly positioning said second shell relative to said first shell, wherein said second connectors are positioned on said plurality of bladders such that each said second connector is positioned for selectively coupling to said associated said first connector for coupling said plurality of bladders to said second shell, wherein said second shell is positioned on said rod such that said second shell is configured for inserting the stump through said top into said sleeve, wherein said inlet valve is positioned in said first tube such that said inlet valve is configured for coupling to the pump positioning the pump for inflating said plurality of bladders for coupling said second shell to the stump positioned in said second shell, wherein said outlet valve is positioned in said first tube such that said outlet valve is configured for releasing the air from said plurality of bladders for decoupling said second shell from the stump positioned in said second shell, wherein said first holes are positioned in said first shell such that said first holes are configured for draining water from said first shell, wherein said second holes are positioned in said second shell such that said second holes are configured for draining water from said second shell, wherein said grip is positioned on said first shell such that said grip is configured for preventing slipping of said first shell on the surface, such as the bathtub and the shower enclosure, wherein said first cutout is positioned in said second shell such that said first cutout is configured for inserting the patella and the femoral condyle of the amputated leg, wherein said second cutout is positioned in said second shell such that said second cutout is configured for flexing of the knee of the amputated leg.

\* \* \* \* \*